(12) United States Patent
Kafka et al.

(10) Patent No.: US 6,373,565 B1
(45) Date of Patent: *Apr. 16, 2002

(54) METHOD AND APPARATUS TO DETECT A FLAW IN A SURFACE OF AN ARTICLE

(75) Inventors: James D. Kafka, Mountain View; Bruce Craig, Los Gatos, both of CA (US)

(73) Assignee: Spectra Physics Lasers, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/321,499

(22) Filed: May 27, 1999

(51) Int. Cl.[7] .............................................. G01N 21/00
(52) U.S. Cl. .............................. 356/237.4; 356/237.1; 356/237.3; 356/237.5; 372/39; 372/67; 372/75
(58) Field of Search ........................... 356/237.1, 237.2, 356/237.4, 237.5, 239.3, 239.7, 239.8; 372/9–10, 18, 20, 22, 39, 69–72, 75, 24

(56) References Cited

U.S. PATENT DOCUMENTS

| | | | |
|---|---|---|---|
| 4,377,340 A | 3/1983 | Green et al. | 356/237 |
| 4,630,276 A | 12/1986 | Moran | 372/15 |
| 4,942,582 A * | 7/1990 | Kintz et al. | 372/18 |
| 4,989,984 A | 2/1991 | Salinger | 356/445 |
| 5,127,726 A | 7/1992 | Moran | 356/237 |
| 5,170,063 A | 12/1992 | Miyazaki et al. | 250/572 |
| 5,177,559 A | 1/1993 | Batchelder | 356/237 |
| 5,394,413 A | 2/1995 | Zayhowski | 372/10 |
| 5,623,341 A | 4/1997 | Hunt | 356/300 |
| 5,627,854 A | 5/1997 | Knox | 372/99 |
| 5,712,701 A * | 1/1998 | Clementi et al. | 356/237.1 |
| 5,812,308 A | 9/1998 | Kafka et al. | 359/346 |
| 5,834,160 A | 11/1998 | Ferry et al. | 430/313 |
| 5,936,983 A * | 8/1999 | Yusong et al. | 372/22 |
| 6,061,370 A * | 5/2000 | Yin | 372/22 |
| 6,157,663 A * | 12/2000 | Wu et al. | 372/75 |
| 6,185,235 B1 * | 2/2001 | Cheng et al. | 372/39 |
| 6,246,706 B1 * | 6/2001 | Kafka et al. | 372/24 |

FOREIGN PATENT DOCUMENTS

| | | | |
|---|---|---|---|
| DE | 195 29 656 A1 | 2/1997 | G03F/7/20 |
| EP | 0 818 858 A2 | 1/1998 | H01S/3/0941 |
| WO | WO 98/33096 | 7/1998 | G03F/1/08 |

\* cited by examiner

Primary Examiner—Frank G. Font
Assistant Examiner—Sang H. Nguyen
(74) Attorney, Agent, or Firm—Wilson Sonsini Goodrich & Rosati

(57) ABSTRACT

An inspection apparatus includes a laser system. The laser system has a high reflector and an output coupler that define an oscillator cavity which produces an output beam. A gain medium and a mode locking device are positioned in the oscillator cavity. A diode pump source produces a pump beam that is incident on the gain medium. An output beam directing apparatus directs the output beam to the surface of the article. A surface flaw at the surface of the article produces scattered light from at least a portion of the output beam incident on the surface flaw. A detector is positioned to detect the scattered light.

60 Claims, 3 Drawing Sheets

METHOD AND APPARATUS TO DETECT A FLAW IN A SURFACE OF AN ARTICLE

CROSS REFERENCE TO RELATED APPLICATIONS

This application is related to U.S. patent application entitled "Laser Writing Method and Apparatus", identified as Ser. No. 09/322,803, filed concurrent herewith; and U.S. Patent Application entitled "Quasi-Continuous Wave Lithography Apparatus and Method", identified as Ser. No. 09/322,121, filed concurrent herewith, which applications are incorporated herein by reference.

BACKGROUND OF THE INVENTION

1. Field of the Invention

This invention relates to a method and apparatus to detect a flaw in a surface of an article, and more particularly to a surface inspection apparatus that uses a diode-pumped, mode-locked laser.

2. Description of Related Art

In the process of manufacturing a silicon microchip, light is directed through a reticle mask to etch circuits into a silicon wafer disc. The presence of dirt, dust, smudges, scratches or other flaws on the surface of the silicon wafer is highly undesirable and will adversely affect the resulting circuits. As a result, the silicon wafers are necessarily inspected prior to and during the manufacturing process. One common inspection technique is for a human inspector to visually examine the surface under intense light and magnification. However, the microscope has a small field of view so it takes a human inspector an extended period of time to visually examine the entire surface of the wafer.

Laser surface inspection devices have been developed for inspecting the surface of polished silicon wafers to accurately detect small particles or flaws. Examples of such devices are disclosed in Alford et al. U.S. Pat. No. 4,376,583 issued Mar. 15, 1983 and Moran U.S. Pat. No. 4,630,276 issued Dec. 16, 1986. In these known laser surface inspection systems, a laser beam is transversed across the surface of the silicon wafer and the reflections from the wafer are collected and analyzed to provide information about any flaws present on the wafer surface. The light is specularly reflected from the polished surface of the wafer, but in locations where the beam strikes surface flaws, the light is scattered. By separately collecting the scattered and specularly reflected light, the inspection device can quickly determine the size and locations of flaws on the surface of the wafer. This provides a satisfactory pass/fail test for inspecting the wafers, however, the nature and source of the flaws are not suitably analyzed by such laser inspection techniques. Also, when the wafer has been etched with a pattern to form the microchips the etching may provide spurious indications of flaws on the surface.

To inspect the patterned surface of silicon wafers, low angle laser surface inspection devices are employed, such as those disclosed in Koizumi et al. U.S. Pat. No. 4,614,427 and Shiba et al. U.S. Pat. No. 4,669,875 for example. These devices inspect the surfaces of patterned wafers using a laser beam at a low glancing angle. However, laser scanning does not provide sufficient resolution or clarity of the flaws to analyze the nature or source of the flaws in the surface.

Optical scanning arrangements are known which use optical lenses to microscopically view the surface and identify and analyze flaws in the surface. However, such systems produce enormous amounts of data and require powerful computers to process and analyze the data produced. Accordingly such systems are very expensive. Because of the small field of view and the enormous volume of data obtained, this type of system is relatively low.

In one recently developed device, Hitachi model HLIS-200, foreign particles are detected by a low angle fixed spot laser beam. As the wafer rotates and translates under the laser beam, the particles are detected by an overhead photomultiplier and a map of the particles is formed. Subsequently, the foreign particles may be microscopically observed and photographed by repositioning the flaw under a microscopic viewing device. However, this requires a very accurate and reliable X-Y table to reposition the flaws in the field of view. Also, the process of inspecting the wafers by moving the wafer around under the fixed spot laser is slow and time consuming.

SUMMARY OF THE INVENTION

Accordingly, an object of the invention is to provide a method and apparatus to inspect a surface of an article.

Another object of the invention is to provide a method and apparatus to detect flaws in a surface of an article.

Yet another object of the invention is to provide a method and apparatus to detect flaws in a surface of an integrated circuit.

Still another object of the invention is to provide a method and apparatus to detect flaws in a surface of an article using a diode-pumped, mode-locked laser.

These and other objects of the invention are achieved in an inspection apparatus that includes a laser system. The laser system has a high reflector and an output coupler that define an oscillator cavity which produces an output beam. A gain medium and a mode locking device are positioned in the oscillator cavity. A diode pump source produces a pump beam that is incident on the gain medium. An output beam directing apparatus directs the output beam to the surface of the article. A surface flaw at the surface of the article produces scattered light from at least a portion of the output beam incident on the surface flaw. A detector is positioned to detect the scattered light.

In another embodiment, the laser system includes a first amplifier.

In another embodiment, a method is provided for detecting flaws in a surface of an article. A diode-pumped laser system is provided that includes an oscillator cavity, a gain medium and a mode locking device positioned in the oscillator cavity. An output beam is produced from the laser system. The output beam is directed to the surface of the article. Light scattered from a flaw on the surface of the article is detected.

DETAILED DESCRIPTION

Figure 1:
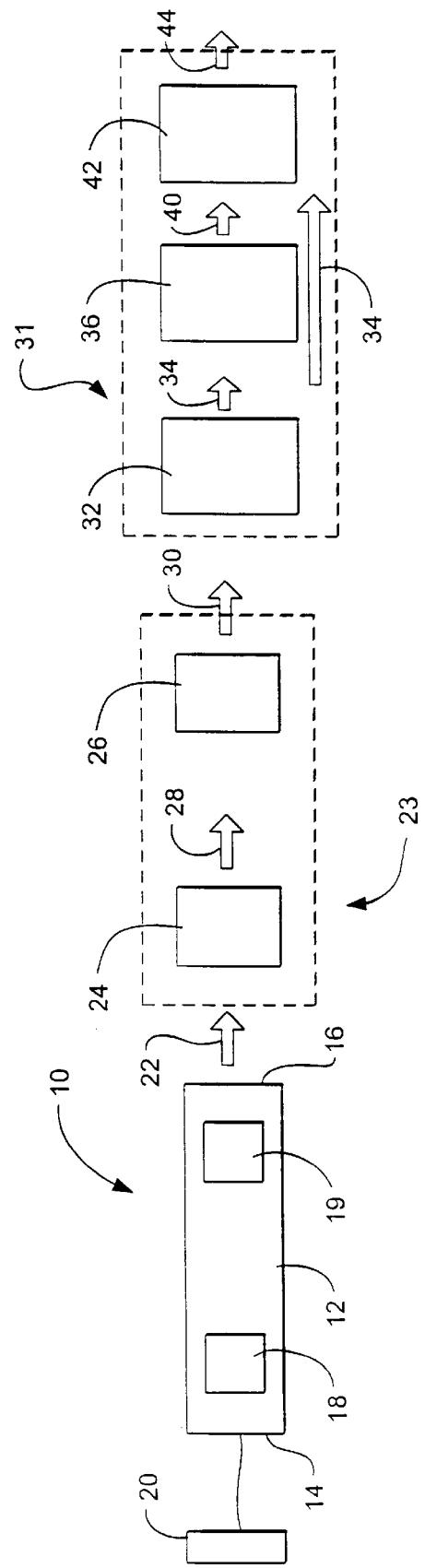
FIG. 1 is a block diagram of a laser, laser/amplifier system useful with the present invention.

The present invention provides an inspection apparatus that includes a laser system. The laser system includes an oscillator system or an oscillator/amplifier system. The oscillator/amplifier system is similar to the oscillator system but includes one or more amplifiers. The oscillator and oscillator/amplifier systems can be coupled with second, third, fourth and fifth harmonic generators. A second harmonic generator can be used alone with the oscillator and oscillator/amplifier systems and in various combinations with third, fourth and fifth harmonic generators. Additionally, the harmonic generators can be coupled with an OPO. The OPO can be pumped by a fundamental beam from an oscillator or from the harmonic generators. An output of the OPO can be mixed with the harmonic generators to generate a variable wavelength source.

In one embodiment, the oscillator system includes an Nd:YVO$_4$ gain media and is mode locked by a multiple quantum well absorber. In a specific embodiment of this oscillator system, the oscillator is pumped by a single fiber-coupled diode bar that provides 13 watts of pump power incident on the Nd:YVO$_4$ gain media, and typically produces 5–6 watts of 5–15 picosecond pulses at 80 MHz repetition rate.

In another embodiment, an oscillator/amplifier system includes an Nd:YVO$_4$ gain media mode locked by a multiple quantum well absorber, a double pass amplifier and two single pass amplifiers. Each of the amplifiers has an Nd:YVO$_4$ gain media and is pumped by two fiber-coupled diode pump sources. This oscillator/amplifier system produces 25–30 watts of 5–15 picosecond pulses at 80 MHz repetition rate.

The oscillator and oscillator/amplifier systems can be mode locked with a multiple quantum well saturable absorber, a non-linear mirror mode locking method, a polarization coupled mode locking method or other mode locking techniques, including but not limited to use of an AO modulator. An example of a quantum well saturable absorber is disclosed in U.S. Pat. No. 5,627,854, incorporated herein by reference. An example of a non-linear mirror mode locking method is disclosed in U.S. Pat. No. 4,914,658, incorporated herein by reference. An example of a polarization coupled mode locking method is disclosed S.N. 09/062,057, filed Apr. 17, 1998, assigned to the same assignee as this application and incorporated herein by reference. In order to producer shorter pulses and a single output beam the gain media is positioned adjacent to a fold mirror as described in U.S. Pat. No. 5,812,308, incorporated herein by reference.

A high power oscillator system with the performance of an oscillator/amplifier system is achieved by using multiple fiber-coupled diodes and either a non-linear mirror mode locking technique or a polarization coupled mode locking method. This high power oscillator system produces 10–20 watts of output power with 4–10 picosecond pulses at a repetition rate of 80–120 MHz. High repetition rates are desirable for applications where the laser system is used as a quasi-CW source. For some applications, 80 MHz repetition rate is sufficiency high to be consider to be quasi-CW. This repetition rate is achieved with an oscillator cavity length of 1.8 meters. When the cavity length is shorted to 0.4 meters the repetition rate increases to 350 MHz.

Referring now to FIG. 1, one embodiment of an oscillator system 10 has a resonator cavity 12 defined by a high reflector 14 and an output coupler 16. A gain media 18 is positioned in resonator cavity 12. Suitable gain media 18 include but are not limited to, Nd:YVO$_4$, Nd:YAG, Nd:YLF, Nd:Glass, Ti:sapphire, Cr:YAG, Cr:Forsterite, Yb:YAG, Yb:glass and the like. A preferred gain media 18 is Nd:YVO$_4$. A mode locking device 19 is positioned in oscillator cavity 12. In the embodiment, oscillator system 10 is mode locked and pumped by a fiber-coupled bar 20 that produces 13 watts of power. Oscillator cavity 12 can produce 1 to 6 watts of power nominally at a 80 MHz repetition rate with pulse widths of 5 to 15 picoseconds.

Optionally included is one or more amplifiers, generally denoted as 23. An output beam 22 from resonator cavity 12 can be amplified by a first amplifier 24. A second amplifier 26 can be included. Additional amplifiers may also be included to increase power. Typically, amplifiers 24 and 26 have the same gain media used in resonator cavity 12. Nd:YVO$_4$ is a suitable gain media material because it provides high gain in an amplifier. The higher gain of Nd:YVO$_4$ provides a simplified amplifier design requiring fewer passes through the gain media. Amplifiers 24 and 26 produce output beams 28 and 30 respectively. Amplifiers 24 and 26 can be single pass, double pass and four pass. A four pass amplifier is disclosed in U.S. Pat. No. 5,812,308, assigned to the same assignee as this application and incorporated herein by reference. Oscillator/amplifier system 10 using an oscillator, a double pass amplifier and two single pass amplifiers can provide 30 watts of average power.

Output beams 22, 28 or 30 can be incident on a harmonic generator generally denoted as 31 and can include a second harmonic generator 32. An output 34 from second harmonic generator 32 can be incident on a third harmonic generator 36 to produce an output beam 40. Output 34 can be incident on a fourth harmonic generator 42 to produce an output beam 44. It will be appreciated that oscillator system 10 can include various combinations of harmonic generators 32, 36, 42 as well as a fifth harmonic generator or an OPO. Second harmonic generator 32 can use non-critically phase matched LBO, third harmonic generator 36 can employ type II LBO and fourth harmonic generator 42 can use type I BBO.

In a specific embodiment, oscillator system 10 includes oscillator cavity 12 with harmonic generation. Output beam 22 is incident on second harmonic generator 32. In this specific embodiment, oscillator system 10 may also include third and fourth harmonic generators 36 and 42. The output power of this oscillator system 10 is 5 watts at 1064 nm. A harmonic generation system produces 2 watts at 532 nm or 1 watt at 355 nm or 200 milliwatts at 266 nm.

In another specific embodiment, Nd:YVO$_4$ is the gain media of oscillator/amplifier system 10, and 29 watts of 7 picosecond pulses at 1064 nm is produced. The harmonic generation system can generate 22 watts at 532 nm or 11 watts at 355 nm or 4.7 watts at 266 mn.

In another specific embodiment, oscillator/amplifier system 10 includes oscillator cavity 12, a four pass amplifier 24 and second harmonic generator 32 to produce 2 watts at 532 nm. This oscillator/amplifier system can pump an OPO that utilizes non-critically phase matched LBO as described in Kafka, et al., J. Opt. Soc. Am. B 12, 2147–2157 (1995) incorporated herein by reference.

In another specific embodiment, oscillator/amplifier system 10 includes oscillator cavity 12, a double pass amplifier 24 and three single pass amplifiers 26 that produces 42 watts of 7 picosecond pulses at 1064 nm. This oscillator/amplifier system can pump an OPO using non-critically phase-matched KTA and produce an output beam at 1535 nm. The output beam at 1535 nm can be mixed with a 1064 nm beam to provide 11.6 watts at 629 nm, as described in Nebel, et al., in *Conference on Lasers and Electro-Optics*, Vol. 6 of 1998 OSA Technical Digest Series (Optical Society of America, Washington, D.C., 1998) postdeadline paper CPD3.

40 watts fiber-coupled bars, commercially available from Opto-Power, Tucson, Ariz. can be used to increase the output power of oscillator or oscillator/amplifier systems 10. The use of an Nd:YVO$_4$ gain media 18 with a doping level of less than 0.5% can also be used to increase the output power of oscillator or oscillator/amplifier systems 10. The combination of the 40 watt fiber-coupled bars with the low doped Nd:YVO$_4$ gain media greatly increases the output power of oscillator and oscillator/amplifier systems 10. Use of low doped Nd:YVO$_4$ gain media 18 can also reduce the sensitivity of oscillator cavity 12 to misalignment as well as improve the output beam quality from an amplifier 24 or 26. The use of low doped Nd:YVO$_4$ gain media, a longer Nd:YVO$_4$ gain media as well as a larger pump volume in Nd:YVO$_4$ gain media is disclosed in commonly owned application Ser. No. 09/199,031, filed Nov. 24, 1998, incorporated herein by reference.

Hereafter, oscillator system and/or oscillator/amplifier system 10, shall collectively be referred to as laser system 110, and output beams 22, 28, 30, 34, 40 or 44 are collectively denoted as output beam 112.

Figure 2:
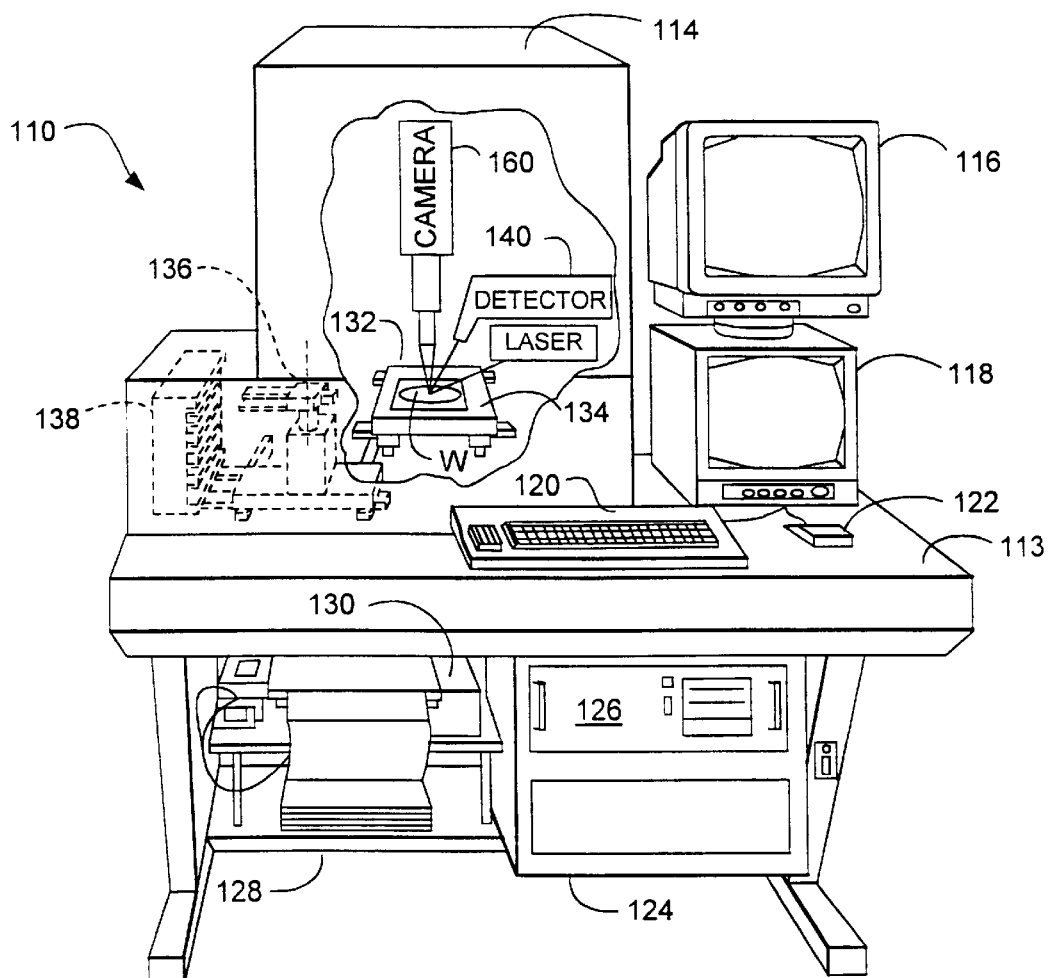
FIG. 2 is a schematic illustration of the system.
Figure 3:
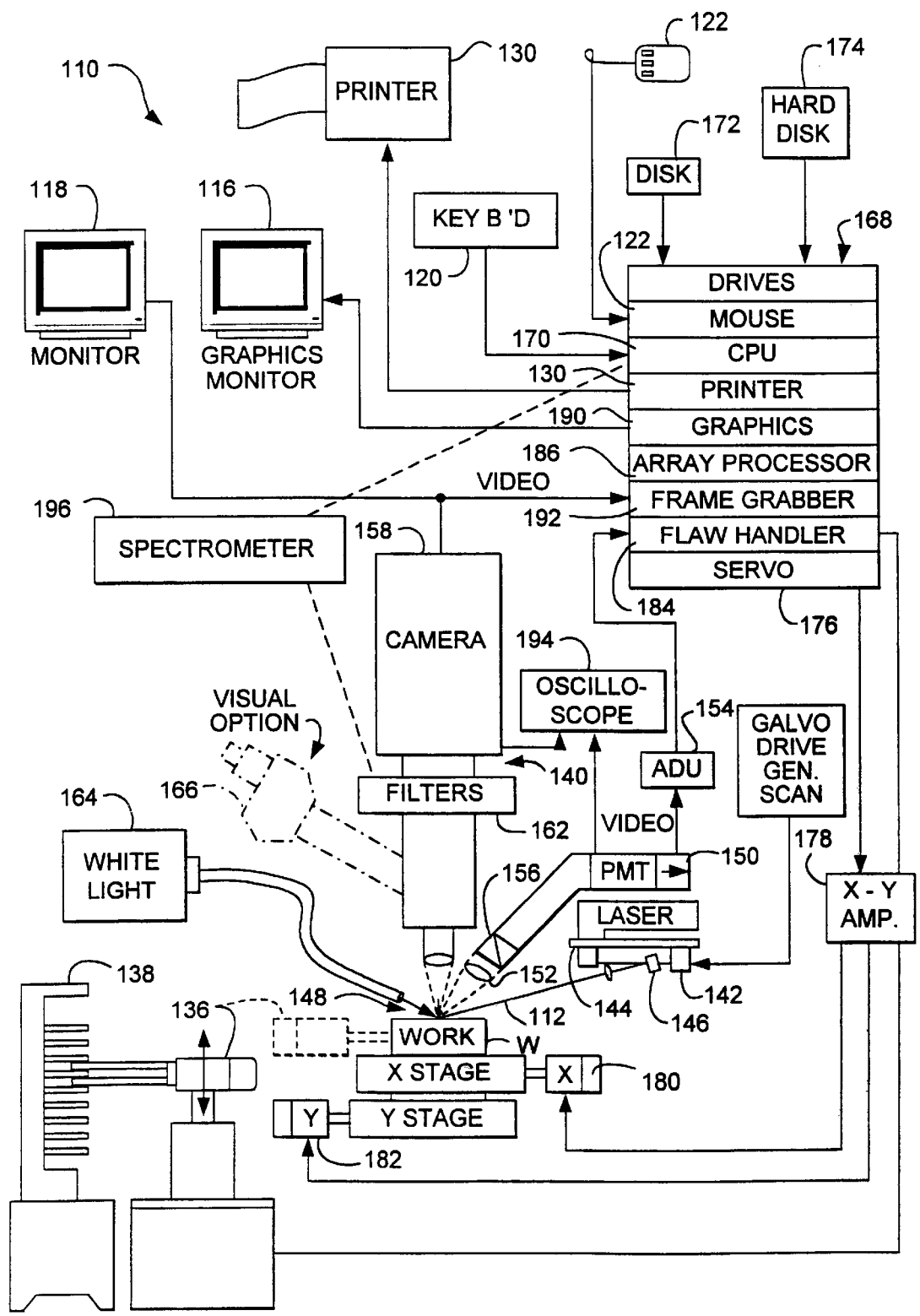
FIG. 3 is an example of the surface inspection system of the present invention.

Referring to FIGS. 2 and 3, surface inspection system 110 is arranged to inspect the surfaces of silicon wafers to detect dirt, dust, smudges, scratches or other flaws. However, inspection system 110 may be utilized for inspecting the surfaces of many types of articles including but not limited to liquid crystal displays and web substrates such as photographic film.

Inspection system 110 is arranged as a workstation and includes a worktable 113. Positioned on worktable 113 is a generally closed and substantially light proof housing 114, a pair of video displays 116 and 118, a keyboard 120 and a mouse 122. A cabinet 124 is suspended below worktable 113 for carrying a system controller 126. Adjacent to cabinet 124 is a shelf unit 128 for carrying a printer 130 and associated printer paper.

Housing 114 has been partially broken away in FIG. 2 to better illustrate the inspection arrangement of the present invention. The inspection of a wafer W is conducted in an inspection station zone 132 on an inspection table 134. Table 134 is an X-Y table which is mounted for precise movement along both the X and Y horizontal axes. In an alternative embodiment table 134 is an X-Y-Z-θ table which is able to move precisely in the X, Y and Z directions as well as being rotated about the vertical Z axis. A robotic wafer handling device 136 is located adjacent to inspection station zone 132 to load and unload wafers from a cassette 138 onto table 134. Cassette 138 holds a number of wafers and is loaded into cabinet 124 through a door (not shown). The handling of wafers inside housing 114 is done automatically without contact by human hands to avoid contamination or smudges.

Inspection of wafer W is accomplished by laser system 110 and an optical inspection system generally indicated by 140. Laser system 110 is arranged to direct output beam 112 through focusing lenses as known in the art to a scanning mirror 142 which deflects output beam 112 along a predetermined oscillating scan pattern. Scanning mirror 142 may be of any suitable type known in the art, including but not limited to a rotating polygonal mirror or, as illustrated, an electrically reciprocated mirror (galvanomirror) driven by a galvo drive.

The scanned output beam is then directed to a folded optical cell that can include mirrors 144 and 146. Mirrors 144 and 146 are configured and arranged to effectively form a collimated scan pattern such that the beam at one part of the scan is essentially parallel to the beam at other parts of the scan. Such a scan pattern is also referred to as a telocentric scan. An example of a suitable folded optic cell is disclosed in U.S. Pat. No. 4,630,276, incorporated herein by reference.

As illustrated in FIG. 3, the folded optical cell is arranged that it directs the scanning output beam to inspection zone 148 at a low angle with respect to the wafer surface in one embodiment, the angle of incidence is approximately 10°. Because the scanned output beam moves in a substantially parallel or telecentric scan pattern as it traverses the wafer surface, the focal length of the beam does not vary significantly and the beam remains in sharp focus throughout the scan.

As output beam 112 is scanned across the surface of wafer W, inspection table 134 moves wafer W at a constant speed perpendicular to the scan line formed by the scanned output beam. The scans of output beam 112 sweep back and forth across the wafer surface as the wafer moves through output beam 112, and the entire surface of wafer W is scanned relatively quickly.

As the surface of wafer W is scanned in inspection zone 148, light is reflected by the wafer surface away from laser system 110 at an angle generally corresponding to the low angle of incidence. However, if the surface has any flaws such as scratches or dirt then the flaws reflect the light in a scatter randomly oriented pattern.

To detect the flaws a light collector 150 is arranged to receive reflect light directed generally back toward laser system 110. Collector 150 includes a lens 152 to focus light to a photomultiplier tube. The photomultiplier tube converts the collected light signals into electrical signals for subsequent processing and analysis. An A/D convertor 154 converts analog signals of the photomultiplier tube to signals for use by system controller 126.

Inspection system 110 may also include in a polarizing lens arranged in the path of the output beam 112 and a polarizing filter 156 arranged in the path of the reflected laser light reaching collector 150. The orientation of polarizing lens filter 156 can be adjusted to assist in filtering out background noise and false flaw signals, such as reflections from the pattern on the surface of the wafer W.

Optical inspection system 140 is arranged directly over inspection station zone 132 with its viewing axis substantially perpendicular to the wafer surface to provide a magnified view of the flaws on the wafer W. Optical inspection system 140 includes a video camera 158 provided with one or more focusing and magnifying lenses 160 with filters 162. Optical inspection system 140 may be operated using the light from laser system 110. However, a white light source 164 may also be provided to give auxiliary illumination for video camera 158. The image received by camera 158 is displayed by video display monitor 118. However, as indicated in broken lines in FIG. 3, inspection system 140 may optionally include a direct view eyepiece 166.

Inspection system 110 is computer controlled by a system controller 126 System controller 126 operates inspection system, stores and retrieves data generated by inspection system 110 and optical inspection system 140 and performs data analysis. As illustrated in FIG. 3, system controller 126 includes many components. System controller 126 includes a main central processing unit 170 with input and output devices including keyboard 120, mouse 122, removable diskette drive 172, hard disk 174, and printer 130.

Figure 4:
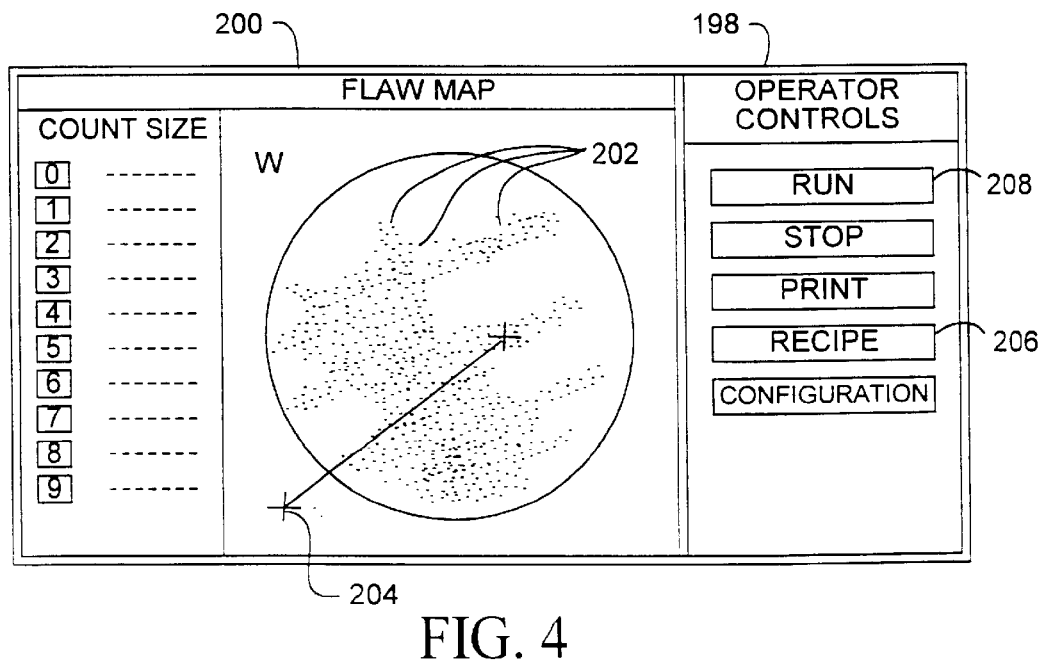
FIG. 4 is an example illustration of a computer display produced by the system.

System controller 126 further includes a servo control board 176 which provides an output signal to a servo amplifier 178 for controlling operation of X and Y axis motors 180, 182 associated with inspection table 134 and for also controlling operation of wafer handling device 136. In addition, system controller 126 includes a flaw handler printed circuit board 184 which receives flaw data from A/D unit 184 and assembles the data into scan lines for use by array processor. The assembled flaw data is transferred to array processor 186 which functions to count the flaws, sort them into user-defined bins, perform edge exclusion, eliminate double-pixeling and assess scratches and haze on the article surface. A high resolution graphics controller 190 assimilates flaw data from CPU 170 and graphically displays, by means of high resolution graphics monitor 116, a flaw map and other operational information regarding inspection system 110 as illustrated in FIG. 4. A frame grabber 192 receives the video image of the wafer from video camera 158 and digitizes the image to be maintained in storage, to be displayed on video monitor 118 or printed onto hard copy paper by printer 130.

System controller 126 also includes system software operable by the user for configuring the system, controlling the motion of wafer handling device 136, inspection and optical inspection systems 110, 140, and presenting the collected data via various user-selectable display screens. Movement between screens and machine control can be performed with the use of pop-up menus which can be operated by mouse 122 and/or by keyboard commands. Data such as flaw counts, wafer matrix, statistics, and wafer classification (i.e. ACCEPT or REJECT) can be presented on graphics monitor 116 or as hard copy output from printer 130. System controller 126 is further adapted to store data by suitable means such as removable diskette drive 172 or hard disk 174 for subsequent recall and analysis. Such data may include, in addition to the data discussed above, the flaw map data obtained from inspection system 110, and digitized images of the flaws obtained from optical inspection system 140, as well as the coordinate locations for the flaws.

The system further includes an oscilloscope 194 used for identifying and verifying flaws so that flaws selected for optical inspection are accurately positioned in the field of view of optical inspection system 140. Oscilloscope 194 has input channels from each of video camera 158 and fiber optic collector 150. Oscilloscope 194 may then compare the signals received by video camera 158 with the signals received from collector 150. The output of oscilloscope 194 is provided on its own display and used by the operator to direct the X-Y table to the correct position of the selected flaw.

Inspection system 110 also has a third level of inspection, after inspection apparatus 126 and optical inspection system 140. Inspection system 140 includes spectrometer 196 to analyze detected flaws based upon the colors of light reflected. Different materials and substances have different and sometimes characteristic color reflections. Identifying the characteristic color of the debris on wafer W may enable the operator to determine whether the debris is harmless or harmful. Also knowing the material may quickly isolate the source of contamination. This data may also be stored by system controller 128 with the data of the coordinates and digitized images of each flaw for subsequent recall, review and analysis.

FIG. 4 illustrates a computer display produced by inspection system 110. The display is provided by graphics monitor 116 which is preferably a color video display monitor. Inspection system 110 includes a highly adaptable graphics display including windowing options to provide maximum adjustability for an operator. FIG. 4 illustrates an operator control display 198 and a flaw map 200. Inspection system 110 may also display flaw information in a histogram or other graphic form. Flaw map 200 is, as discussed above, generated from flaw data generated by inspection system 110. The map includes a general representation of the surface of the wafer W with the flaws indicated each by dots 202. Alternatively dots 202 may be indicated by various colors or shapes (such as stars, squares, triangles, etc.) depending on the size or other feature of the flaw. The operator selects a particular flaw on the flaw map by pointing to the flaw with cursor 204. Cursor 204 is moved by moving mouse 122 around on worktable 113. Once a particular location is selected, one of the buttons on the mouse is pressed to indicate to inspection system 110 the particular selection. For example, cursor 204 is illustrated in broken lines pointing out a particular location on the wafer W for closer inspection. Cursor 204 may also be used to push the buttons in operator control display 198 by pointing with cursor 204 similar to selecting a flaw.

The operation of inspection system 110 begins with placing cassette 138 of wafers w in housing 114. The operator instructs inspection system 110 to inspect according to a particular recipe (operating parameters). The recipe may be previously stored on a disk and generally includes such data as the size and thickness of the object being inspected, flaw categories to be detected, and other variables regarding the inspection process. In most cases the recipes will be standardized and stored on hard disk 174 under identifying recipe names. The various recipes are by the operator by pressing recipe button 206 on operator control display 198.

The inspection process begins by the operator pressing a run button 208 on operator control display 198. System controller 168 then directs wafer handling device 136 to load the first wafer from cassette 138 onto inspection table 134. Inspection system 110 is activated and inspection table 134 transports wafer W along inspection station zone 132 until the entire surface has been scanned. The flaw data generated from inspection system 110 is sorted, analyzed, and stored by system controller 168 to generate a flaw map. The flaw map is displayed on graphics monitor 116 in a form similar to that shown in FIG. 4 indicating the flaws and their respective locations.

The operator, using mouse 122, may then select a particular flaw from the flaw map for closer inspection by moving mouse 122 so as to position cross hair cursor 204 onto the selected flaw and then clicking one of the mouse buttons. In response to this selection, system controller 126 actuates the X-Y axis motors 180, 182 associated with inspection table 134 to move the table as necessary along the X and Y axes in order to locate the coordinates of the selected flaw within the field of view of the lens of optical inspection system 140. As the coordinates of the selected flaw approach the field of view of optical inspection system 140, inspection system 110 scans the wafer surface to verify that the selected flaw is accurately positioned in the field of view. An oscilloscope 194 also may be used by the operator to verify that the selected flaw is centered in the field of view.

Alternatively system controller 126 may separately verify the flaw location. The stored data for the selected flaw includes the precise data for the scan which detected the flaw. By comparing the stored data of the scan with the current scan being directed across the wafer the selected flaw would then be identified by the current scan. At the same time, system controller 126 monitors the light signals received by each of video camera 158 and collector 150. System controller 126 can very quickly bring the selected flaw into the field of view of the camera by comparing the timing of the two signals with oscilloscope 194. If the reflected light entering camera 158 is coincident with the timing of the reflected light from the selected flaw, then the selected flaw is in the field of view of camera 158. If the timing is not coincident, then inspection table 134 needs to adjust the position of wafer W. Once inspection system 110 detects the selected flaw, system controller 126 quickly directs inspection table 134 to provide the flaw in the field of view as before.

After the optical analysis of each flaw, the flaw may then be spectrometrically analyzed by spectrometer 196. Spectrometer 196, in cooperation with optical inspection system 140, analyzes the color spectrum of white light reflected by the selected flaw. The results of the spectrometric breakdown of the light are provided to system controller 126 for further analysis, comparison and storage. This provides information characterizing the flaw in addition to the optical inspection.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An inspection apparatus to inspect a surface of an article, comprising:
   a laser system including a high reflector and an output coupler defining an oscillator cavity that produces an output beam, a gain medium with a doping level of less than 0.5%, and a mode locking device positioned in the oscillator cavity and a diode pump source producing a pump beam incident on the gain medium;
   a scanning mirror that directs the output beam to the surface of the article, wherein a surface flaw at the surface produces scattered light from at least a portion of the output beam incident on the surface flaw; and
   a detector positioned to detect the scattered light.

2. The system of claim 1, wherein the scanning mirror is a rotating mirror.

3. The system of claim 1, wherein the gain medium is Nd:YVO$_4$, Nd:YAG, Nd:YLF, Nd:Glass, Ti:sapphire, Cr:YAG, Cr:Forsterite, Yb:YAG and Yb:glass.

4. The system of claim 1, wherein the gain medium is Nd:YVO$_4$.

5. The system of claim 1, wherein the diode pump source is fiber coupled.

6. The system of claim 1, wherein the mode locking device is a multiple quantum well saturable absorber.

7. The system of claim 1, wherein the mode locking device is a non-linear mirror mode locker.

8. The system of claim 1, wherein the mode locking device is a polarization coupled mode locker.

9. The system of claim 1, wherein the mode locking device is an acousto-optic modulator.

10. The system of claim 1, wherein the output beam has a power of 10 watts or greater.

11. The system of claim 10, wherein the output beam is pulsed at 4–10 picoseconds.

12. The system of claim 11, wherein the output beam has a repetition rate of 80–120 MHz.

13. The system of claim 10, wherein the output beam is pulsed at 4–10 picoseconds.

14. The system of claim 13, wherein the output beam has a repetition rate of 80–120 MHz.

15. The system of claim 1, further comprising:
    a second harmonic generator coupled to the oscillator cavity.

16. The system of claim 15, further comprising:
    a third harmonic generator coupled to second harmonic generator.

17. The system of claim 16, wherein the third harmonic generator is made of type II LBO.

18. The system of claim 16, wherein the third harmonic generator is made of type II LBO.

19. The system of claim 15, further comprising:
    a fourth harmonic generator coupled to the second harmonic generator.

20. The system of claim 19, wherein the fourth harmonic generator is made of type I BBO.

21. The system of claim 15, further comprising:
    a fourth harmonic generator coupled to the second harmonic generator.

22. The system of claim 21, wherein the fourth harmonic generator is made of type I BBO.

23. The system of claim 1, wherein the second harmonic generator is made of LBO.

24. An inspection apparatus to inspect a surface of an article, comprising:
    a laser system including a high reflector and an output coupler defining an oscillator cavity that produces an output beam, a gain medium with a doping level of less than 0.5%, and a mode locking device positioned in the oscillator cavity and a diode pump source producing a pump beam incident on the gain medium;
    means for moving the article relative to the output beam; and
    a detector positioned to detect the scattered light.

25. An inspection apparatus to inspect a surface of an article, comprising:
    a laser system including a high reflector and an output coupler defining an oscillator cavity that produces an output beam, a gain medium and a mode locking device positioned in the oscillator cavity, a fiber coupled diode pump source producing a pump beam incident on the gain medium and a first amplifier;
    means for moving the article relative to the output beam; and
    a detector positioned to detect the scattered light.

26. An inspection apparatus to inspect a surface of an article, comprising:
    a laser system including a high reflector and an output coupler defining an oscillator cavity that produces an output beam, a gain medium and a mode locking device positioned in the oscillator cavity, a fiber coupled diode pump source producing a pump beam incident on the gain medium and a first amplifier;
    a scanning mirror that directs the output beam to the surface of the article, wherein a surface flaw at the surface produces scattered light from at least a portion of the output beam incident on the surface flaw; and
    a detector positioned to detect the scattered light.

27. The system of claim 26, wherein the scanning mirror is a rotatable mirror.

28. The system of claim 26, wherein the gain medium is Nd:YVO$_4$, Nd:YAG, Nd:YLF, Nd:Glass, Ti:sapphire, Cr:YAG, Cr:Forsterite, Yb:YAG and Yb:glass.

29. The system of claim 26, wherein the gain medium is Nd:YVO$_4$.

30. The system of claim 26, wherein the mode locking device is a multiple quantum well saturable absorber.

31. The system of claim 26, wherein the mode locking device is a non-linear mirror mode locker.

32. The system of claim 26, wherein the mode locking device is a polarization coupled mode locker.

33. The system of claim 26, wherein the mode locking device is an acousto-optic modulator.

34. The system of claim 26, wherein the output beam has a power of 10 watts or greater.

35. The system of claim 26, further comprising:
a second harmonic generator coupled to the first amplifier.

36. The system of claim 35, further comprising:
a third harmonic generator coupled to second harmonic generator.

37. The system of claim 26, wherein the second harmonic generator is made of LBO.

38. The system of claim 26, further comprising:
a second amplifier coupled to the first amplifier.

39. The system of claim 26, further comprising:
a second harmonic generator coupled to the first amplifier.

40. The system of claim 39, further comprising:
a third harmonic generator coupled to second harmonic generator.

41. The system of claim 39, further comprising:
a fourth harmonic generator coupled to the second harmonic generator.

42. A method of inspecting a surface of an article, comprising:
providing a diode pumped laser system including an oscillator cavity, a gain medium with a doping level of less than 0.5% and a mode locking device positioned in the oscillator cavity;
producing an output beam from the laser system;
directing the output beam to the surface of the article; and
detecting light scattered from a flaw on the surface of the article.

43. The method of claim 42, wherein the output beam is scanned across the surface of the article.

44. The method of claim 43, further comprising:
exposing a selected area of the surface of the article to the output beam.

45. The method of claim 42, further comprising:
passing the output beam through a beam expander.

46. The method of claim 42, further comprising:
focussing the output beam onto the surface of the article.

47. The method of claim 42, wherein the article is an integrated circuit.

48. The method of claim 42, wherein the gain medium is $Nd:YVO_4$.

49. The method of claim 48, wherein the laser/amplifier system includes a second amplifier.

50. The method of claim 42, wherein the laser is a fiber coupled diode pumped laser.

51. The method of claim 42, wherein the mode locking device is a multiple quantum well saturable absorber.

52. The method of claim 42, wherein the mode locking device is a non-linear mirror mode locker.

53. The method of claim 42, wherein the mode locking device is a polarization coupled mode locker.

54. The method of claim 42, wherein the mode locking device is an acousto-optic modulator.

55. The method of claim 42 wherein the output beam has a power of 10 watts or greater.

56. The method of claim 55, wherein the output beam is pulsed at 4–10 picoseconds.

57. The method of claim 56, wherein the output beam has a repetition rate of 80–120 MHz.

58. The method of claim 42, wherein the laser system further includes a harmonic generator device.

59. The method of claim 42, wherein the laser system is a laser/amplifier system that includes a first amplifier.

60. The method of claim 59, wherein the laser/amplifier system includes a harmonic generator device.

* * * * *